United States Patent
Leonhardt

(10) Patent No.: US 6,572,645 B2
(45) Date of Patent: Jun. 3, 2003

(54) DELIVERY SYSTEM FOR DEVELOPMENT AND ENDOVASCULAR ASSEMBLY OF A MULTI-STAGE STENTED GRAFT

(75) Inventor: Howard J. Leonhardt, Davie, FL (US)

(73) Assignee: Medtronic Ave, Inc., Santa Rosa, CA (US)

( * ) Notice: Subject to any disclaimer, the term of this patent is extended or adjusted under 35 U.S.C. 154(b) by 0 days.

(21) Appl. No.: 09/909,631

(22) Filed: Jul. 19, 2001

(65) Prior Publication Data

US 2002/0029075 A1 Mar. 7, 2002

Related U.S. Application Data

(62) Division of application No. 09/257,757, filed on Feb. 25, 1999, now Pat. No. 6,280,467.
(60) Provisional application No. 60/076,383, filed on Feb. 26, 1998.

(51) Int. Cl.[7] .................................................. A61F 2/06
(52) U.S. Cl. ...................................... 623/1.11; 606/194
(58) Field of Search .............................. 623/1.11, 1.12, 623/1.13, 1.16; 606/194

(56) References Cited

U.S. PATENT DOCUMENTS

| 5,709,701 A | * | 1/1998 | Parodi ........................ 606/194 |
| 5,713,917 A | * | 2/1998 | Leonhardt et al. .......... 606/194 |
| 5,733,325 A | * | 3/1998 | Robinson et al. ............... 623/1 |
| 5,860,998 A | * | 1/1999 | Robinson et al. ........... 606/194 |
| 6,102,940 A | * | 8/2000 | Robichon et al. ............... 623/1 |
| 6,123,723 A | * | 9/2000 | Konya et al. .............. 623/1.11 |

* cited by examiner

*Primary Examiner*—David H. Willse
*Assistant Examiner*—Javier G. Blanco

(57) ABSTRACT

A multi-stage stent graft for implantation into a blood vessel is disclosed. Each stage or layer may comprise radially compressible spring stents with or without a fabric covering, or may comprise a foamed tube. The various stages or layers may also have an adhesive coated thereon. The multi-stage stented graft and the adhesive coatings provide a surface for the ingrowth of cells and promote healing. Also disclosed is a coaxial delivery system for the delivery and endovascular assembly of the multi-stage stented graft during one trip into the vasculature.

13 Claims, 5 Drawing Sheets

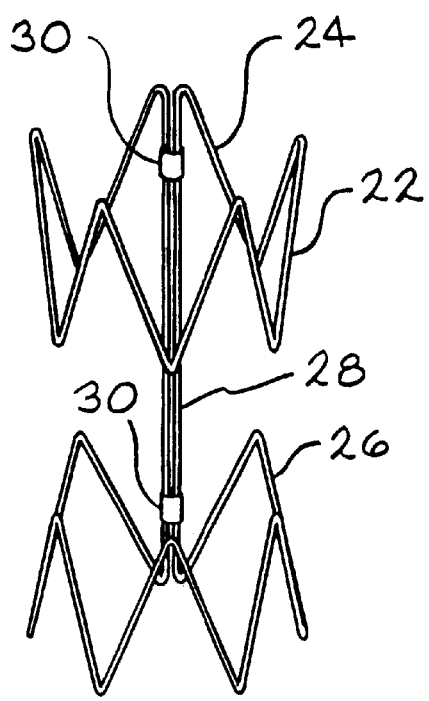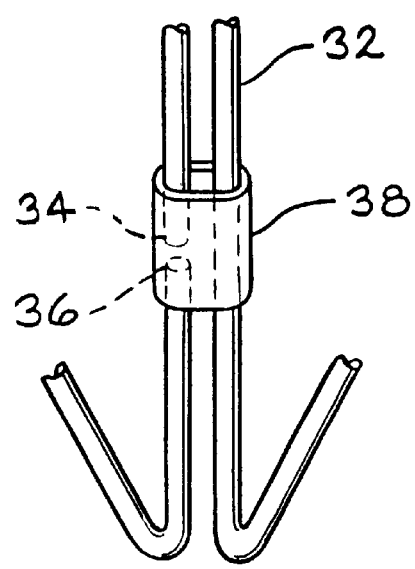
FIG. 2C
FIG. 2D

DELIVERY SYSTEM FOR DEVELOPMENT AND ENDOVASCULAR ASSEMBLY OF A MULTI-STAGE STENTED GRAFT

CROSS-REFERENCE TO RELATED APPLICATION

This application is a division of prior U.S. application Ser. No.: 09/257,757 filed Feb. 25, 1999 now U.S. Pat. No. 6,280,467 which claims the benefit of provisional No. 60/076,383 filed Feb. 26, 1998.

BACKGROUND OF THE INVENTION

1. Field of the Invention

The present invention generally relates to the area of blood vessel graft systems. More particularly, the present invention provides a catheter base delivery device for deployment of multi-stage stented grafts comprising multiple coaxial delivery mechanisms. The coaxial delivery device enables the multiple stages of a stented graft to be assembled endovascularly.

2. Description of the Related Art

Aortic aneurysms are a common type of deteriorating disease caused by weakening of the wall of a blood vessel. The weakened wall, under the pressure of flowing blood, balloons outward. Such a deformity in the wall of a blood vessel not only affects its ability to conduct blood but is also potentially fatal if a rupture occurs at the site of the aneurysm.

Traditionally, the treatment for aneurysms entailed removing part or all of the aneurysm and implanting a replacement prosthetic section into the lumen. Alternatively, a synthetic or biomaterial graft is sutured end-to-end completely replacing the excised portion of the blood vessel. However, surgical treatment or removal of the aneurysm involves significant invasive techniques, extended hospitalization and associated risk of complications. Complications include extensive blood loss, respiratory tract infections, wound infections, and renal failure. In addition, the mortality rates (8%) are significant for such surgeries.

A more contemporary method of treatment of aneurysms is to place a graft within the lumen of the weakened blood vessel via a catheter based device. Conventional tubular aortic replacement sections, however, are generally larger in diameter than the femoral artery and therefore can not be inserted through the lumen of the femoral artery. The basic concept of a transluminal placement of an endovascular prosthesis for decreasing risk associated with the surgical repair of aortic aneurysms was proposed by Dotter (1969, *Invest Radiol.* 4:329–332). Since then, several investigators have studies the feasibility of different endovascular devices. For example Lazarus (U.S. Pat. No. 5,669,936) discloses a graft system having a capsule catheter that is deployed after femoral arteriotomy. To date, stent-grafts used clinically for treatment of abdominal and thoracic aortic aneurysms have required 18-F to 30-F delivery systems. The large size of the delivery system necessitated surgical femoral arteriotomy and sometimes retroperitoneal left iliac arteriotomy or distal aorta aortotomy, general anesthesia, and high levels of multidisciplinary cooperation. Occasionally, relatively healthy iliac vessels with large diameters are needed or in patients with highly sclerotic tortuous iliac arteries, angioplasty with or without stenting was necessary for performance of endovascular grafting. None of the clinically used devices is suitable for percutaneous insertion; all require a femoral arteriotomy because of their size.

Recently, a catheter based system for the delivery of grafts for repair of aortic aneurysms was disclosed in U.S. Pat. Nos. 5,713,917 and 5,591,195. The system includes a single stage graft comprised of two Nitinol springs. The two Nitinol springs are in physical communication with each other via a Nitinol connecting bar and are embedded in graft material at each end and covered completely by material so as to prevent direct exposure to bodily fluids or tissues. The graft is deployed by using an elongated sheath introducer having an axially extending sheath passage for receiving the graft and maintaining it in a compressed condition. A flexible push rod around the insertion catheter and within the sheath passage is used to push the graft out of the sheath during deployment.

In theory, one way to decrease the size of an endovascular device is to deploy the stented graft as separate parts. However, none of the delivery devices available are suitable for delivery of a multi-stage stented graft by a single percutaneous insertion. There is thus, an ongoing need for graft delivery devices for treatment of aneurysms which requires minimal preparation and hospitalization.

SUMMARY OF THE INVENTION

The present invention provides a multi-stage stented graft that is easily introduced and implanted by percutaneous insertion for the treatment of aneurysms, and which circumvents the need for suturing or stapling to the wall of the blood vessel. The various stages of the stented graft are assembled endovascularly. Accordingly, it is an object of the invention to provide a multi-stage stented graft for implantation into blood vessels.

Another object of the present invention is to provide a multiple-stage stented graft that does not have any barbs or hooks for anchoring to the wall of the blood vessel.

Still another object of the present invention is to provide a delivery device for a multi-stage stented graft that requires a single percutaneous insertion.

Yet another object of the present invention is to provide a method for deployment of a multi-stage stented graft using a multiple coaxial delivery device, wherein the stented graft is assembled endovascularly from the multiple stages.

A still further object of the present invention is that the stented graft serves as a substrate for the growth of cells, lining the lumen of the blood vessels in the area of an aneurysm.

These and other aspects of the present invention will become more apparent to those skilled in the art by reference to the following description and to the appended drawings.

BRIEF DESCRIPTION OF THE DRAWINGS

FIG. 2C is a perspective view of the supporting frame 22 of the first stage of the stented graft shown in FIG. 1.

FIG. 2D is a magnified view of a portion of the supporting frame 22 shown in FIG. 1C illustrating the use of a single Nitinol wire for creating the frame.

DETAILED DESCRIPTION OF THE INVENTION

Since endovascular stented grafts must meet certain strength and durability requirements, the goal of reducing their size profile by decreasing the size of their components is limited. By assembling the components of a stented graft endovascularly, the size of the delivery device is reduced without compromising flexibility. In that respect, the first embodiment of a stented graft of the present invention will be described in detail herein as a two-stage device. However, the present invention is not intended to be so limited and those skilled in the art after having read this specification will readily recognize that two or more stages are within the scope of the present invention. A delivery device for the stented graft is also described. The delivery device enables the stented graft to be introduced into the vasculature through a single percutaneous insertion for subsequent endovascular assembly.

Figure 1:
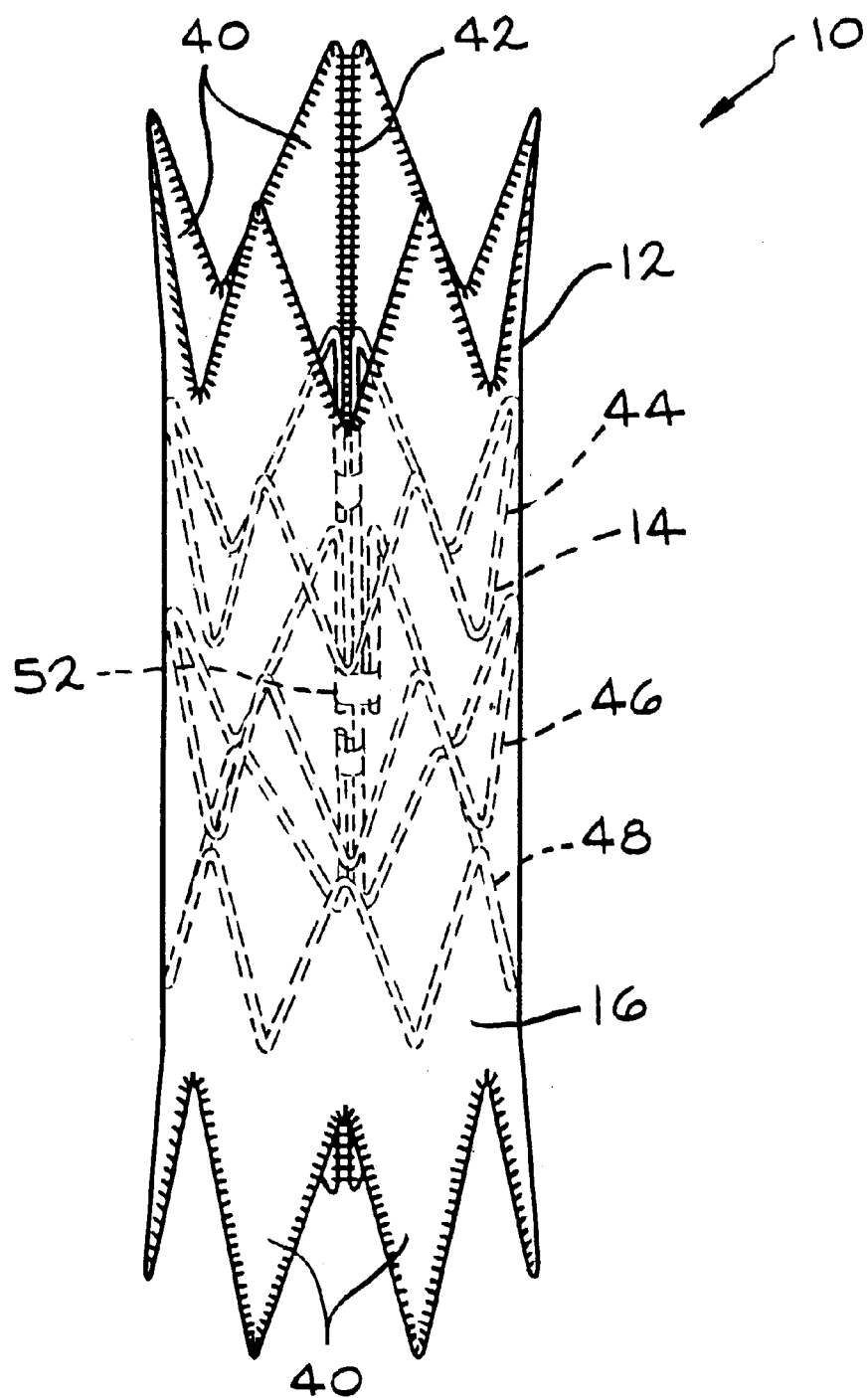
FIG. 1 is a perspective view of a two-stage stented graft 10 of the present invention.
Figure 2A:
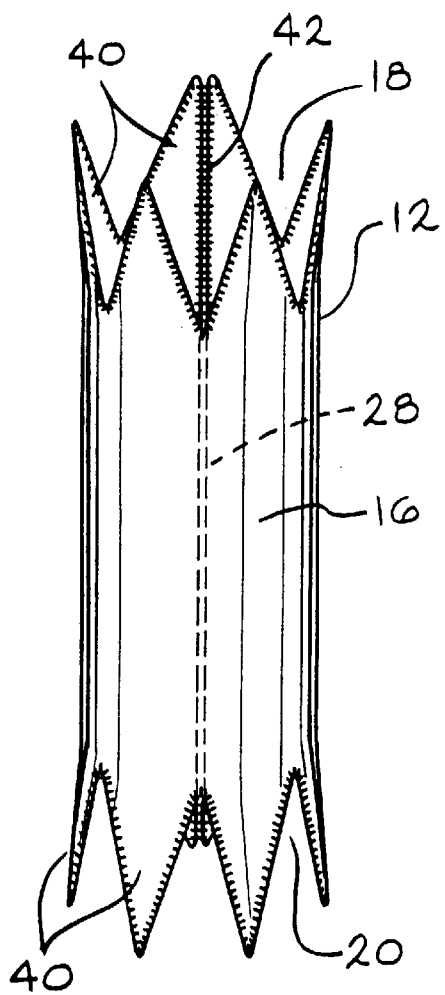
FIG. 2A is a perspective view of a first stage anchoring stent 12 of the two-stage stented graft shown in FIG. 1.
Figure 2B:
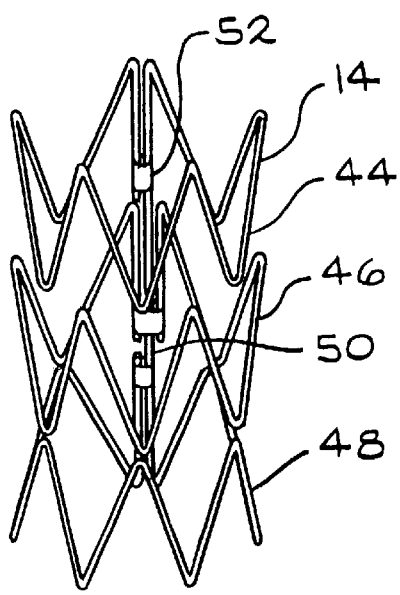
FIG. 2B is a perspective view of a second stage scaffolding stent 14 of the two-stage stented graft shown in FIG. 1.

Turning now to the drawings, FIG. 1 shows a fully assembled two-stage stented graft 10 according to the present invention comprising a first stage anchoring stent 12 (FIG. 2A) and a second stage scaffolding stent 14 (FIG. 2B). The anchoring stent 12 comprises a tubular graft 16 having an annular side wall extending to opposed open ends 18 and 20 and a support frame 22 (FIG. 2C). The synthetic material for the tubular graft 16 is pliable enough to substantially conform to the interior surface of a blood vessel being treated. Suitable synthetic materials include, but are not limited to, woven polyester, polytetrafluoroethylene (PTFE), microporous urethane, nylon and lycra. A preferred fabric material is polyester.

The support frame 22 comprises a spaced apart first stent 24 and a second stent 26 connected to each other by a longitudinal bar 28. If desired, more than one connecting bar is provided. The stents 24 and 26 and the connecting bar 28 can be made as separate parts that are subsequently secured to each other by bands 30 or by welding and the like. If desired, the first and second stents 24, 26 and the intermediate connecting bar 28 can be made of a single wire 32 that is bent or otherwise formed to shape with its terminal ends 34 and 36 (shown in dashed lines in FIG. 2D) disposed proximate to each other and secured in place by a metal band 38. The ends of the wire 32 can also be welded together to complete the construction. In a preferred embodiment of the present invention, the stage one anchoring stent 12 has the first stent 24 located at one of the open ends 18 of the tubular graft 16 while the second stent 26 is located at the other open end 20 with the connecting bar 28 extending therebetween.

In that respect, the tubular graft 16 is initially provided as a sheet or cloth of the synthetic material cut to shape having a plurality of spaced apart flaps or petals 40 extending from each end. The synthetic graft material is formed into the tubular shape by sewing or otherwise securing the sides together along a seam 42. The flaps 40 are sized to cover the peaks and troughs of the respective stents 24 and 26. The tubular graft 16 is then secured to the support frame 22 by sewing the flaps 40 to cover the peaks and troughs of the first and second stents 24 and 26. Examples of methods of sewing the stents within the graft material are disclosed in U.S. Pat. No. 5,713,917 to Leonhardt et al., which patent is hereby incorporated by reference.

The second stage of the two-stage stented graft 10, termed the scaffolding stent 14, is also made of a plurality of radially compressible spring stents, for example stents 44, 46 and 48 connected by connecting bars 50. The scaffolding stent 14 preferably fits longitudinally between the first and second stents 24 and 26 of the first stage anchoring stent 12. The stents 44, 46 and 48 and the connecting bars 50 may be made as a unitary member from one wire in a similar manner as the support frame 22 shown in FIG. 2C or the anchoring stent 14 may be made of separate parts secured together by bands 52, welds and the like. The scaffolding stent 14 may be uncovered or it may be enclosed in a thin polyester covering similar to the tubular graft 16. While not intending to be bound by any particular theory, it is believed that covering both the support frame 22 and the scaffolding stent 14 with, for example, a synthetic material decreases the permeability of the stented graft 10 for abdominal aortic aneurysm treatment and the like. It is important to note that neither the support frame 22 of the anchoring stent 12 or the inner scaffolding stent 14 are equipped with barbs.

Preferably, the first and second serpentine stents 24 and 26 and the intermediate connection bar 28 comprising the support frame 22 of the first stage anchoring stent 12 and the second stage scaffolding stent 14 are made of the nickel-titanium alloy Nitinol. Nitinol is a biologically inert alloy which possesses special shape-memory properties. The alloy is made of approximately equal amounts of nickel and titanium. The shape-memory properties of Nitinol enable the various stents to be initially fabricated into a desired shape and configuration and then, just prior to deployment, collapsed into a shape that fits inside the respective catheters of the delivery device of the present invention for transport through the vasculature. When the stented graft 10 is positioned at the location of a damaged portion of the vasculature, such as an aortic aneurysm and the like, the various Nitinol stents are deformable into their initial fabricated configurations. In that respect, Nitinol is an alloy typically stable at room and body temperature, but that can be stressed to lose its malleability and then permanently revert to its initially fabricated configuration. The transition temperature of the alloy is controlled by varying the composition and processing of the alloy, as is well known by those skilled in the art.

In another embodiment of the present invention, a photopolymerization technique is used to treat the synthetic material of the tubular graft 16. While not intending to be bound by any particular theory, it are believed that photopolymerization makes the surface of the synthetic material conducive to bonding of proteins which are necessary to create a collagen rich surface thereon. This enables a thinner, higher porosity fabric to be utilized without bleed-through and also promotes healing. In addition, cryogenically preserved biological materials, for example, veins including umbilical cord veins, can also be used in lieu of the synthetic graft material. Further, selection of the synthetic graft material depends upon the site of implantation. For example, polyester (Dacron) is preferred for the aortic wall which experiences a higher pressure change than for example, the iliac artery where, PTFE is the preferred material.

In another preferred embodiment of the present invention, the stented graft comprises three stages. In the three stage embodiment, the total thickness is about 0.18 mm measuring in a radial direction extending from the longitudinal axis of the stented graft, with each stage layer being about 0.06 mm thick. The second stage comprises the scaffolding stent 14 having multiple stents connected by a connecting bar. The longitudinal dimensions of the second stage scaffolding stent are such that when it is deployed within the support frame 22 of the anchoring stent 12, the scaffolding stent fits into the space between the first and second stents 24, 26 of the first stage. The distance between each of the five stents comprising the support frame 22 and the scaffolding stent 14 in the assembled stented graft 10 is approximately 5 mm.

The third stage is similar to the first stage and comprises spaced apart first and second stents connected to each other by a connecting bar. The third stage does not require a tubular graft, although if desired, one can be provided. The third stage fits inside the second stage with the first or upper stent spanning between and partially overlapping the first stent 22 of the anchoring stent 12 and the first stent 44 of the scaffolding stent 14 while the second or lower stent spans between and partially overlaps the second stent 26 of the first stage and the third stent 48 of the scaffolding stent. That way, the third stage provides additional supporting structure to the stented graft of the present invention to insure an open and unobstructed lumen therethrough. A further embodiment has the first stent of the third stage intermediate, but not overlapping the stents 22, 44 and the second stent intermediate, but not overlapping the stents 26, 48.

The second stage, which forms the backbone of the assembled graft, may be bare or covered with a synthetic fabric. The fabric covering the various stages may be made of stretchable or non-stretchable materials. In a preferred embodiment, the synthetic fabric covering the first stent is made of a stretchable material enabling the first and second stents to conform to the inner diameter of the wall of the vessel being repaired to prevent any leaks around the edges of the graft. The second and the third stages are preferably made of non-stretchable material to provide strength around the area of the aneurysm. When assembled, the first stage forms the outermost layer, the second stage forms the middle layer and the third stage forms the innermost layer and is exposed to the lumen of the vessel.

Figure 4A:
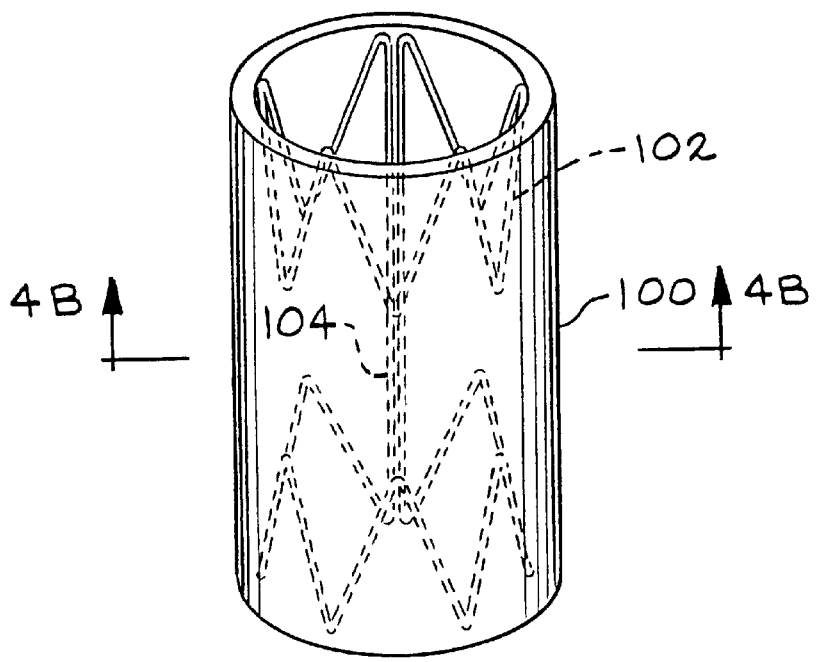
FIG. 4A is a perspective view of a hollow foamed tube 100.
Figure 4B:
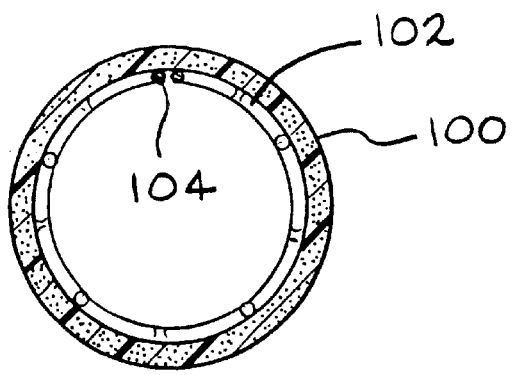
FIG. 4B is a cross-sectional view along line 4B—4B of FIG. 4A.

Another preferred embodiment according to the present invention comprises a three-stage stented graft wherein the first stage is formed by a hollow foamed tube 100 (FIG. 4A) of a closed cell thermoplastic material, as shown in FIG. 4B. It is preferable to have at least one stent 102 provided at the distal open end of the foamed tube to enable easy release of the tube during deployment. More preferably, a stent 102 is provided at each end with at least one connecting wire extending therebetween. The longitudinal support may be a Nitinol wire extending along the length of the foamed tube. The second stage is similar to the support frame 22 of the first stage and comprises two spaced apart stents and a connecting bar. The third stage is a scaffolding stent similar to the second stage shown in FIG. 2B and comprises multiple connected stents that fit between the first and the second stents of the second stage. If a fourth stage is provided, it is similar to the previously described second stage support frame.

In another preferred embodiment of the present invention, a light activated adhesive is coated between the layers or stages of the stented graft. Suitable adhesives include fibrin glue and isobutyl 2 cyanoacrylate. For example, in the previously described two-stage and three-stage stented grafts, fibrin glue is coated on the external surface of the scaffolding stent 14. The adhesive may be released in vivo as described in the previously referenced U.S. Pat. No. 5,713,917 to Leonhardt et al. In a three-stage or a four-stage stented graft comprising an outer foam layer, the fibrin glue is preferably also applied to the top and bottom portions on the external surface of the foam layer so as to form a tight seal with the wall of the blood vessel. While not intending to be bound by any particular theory, it is believed that the multiple layers provide means for the ingrowth of cells from the blood vessel wall into the graft. The fibrin coating facilitates the attachment and growth of the cells thus strengthening the graft.

The multi-stage stented grafts of the present invention may be deployed using delivery devices of the type shown and described in the previously referenced U.S. Pat. No. 5,713,917 to Leonhardt et al. and U.S. Pat. No. 5,591,195 to Taheri et al., which is hereby incorporated herein by reference. Using those delivery devices, the various stages of the stented graft 10 can be deployed in the artery using successive trips into the vasculative. If delivered separately, it is preferable that all of the stages are deployed without delay, otherwise thrombosis may occur between the graft material and aortic wall as well as intraluminally between the pleats of the partially expanded graft material. A clot formation may decrease the lumen of the graft itself, be a source of distal embolization and jeopardize patency of aortic side branches, which is critically important for treatment of thoracic aortic aneurysms. Recatheterization of the lumen of the graft material is time consuming and may even cause the migration of the previously deployed part.

Figure 3:
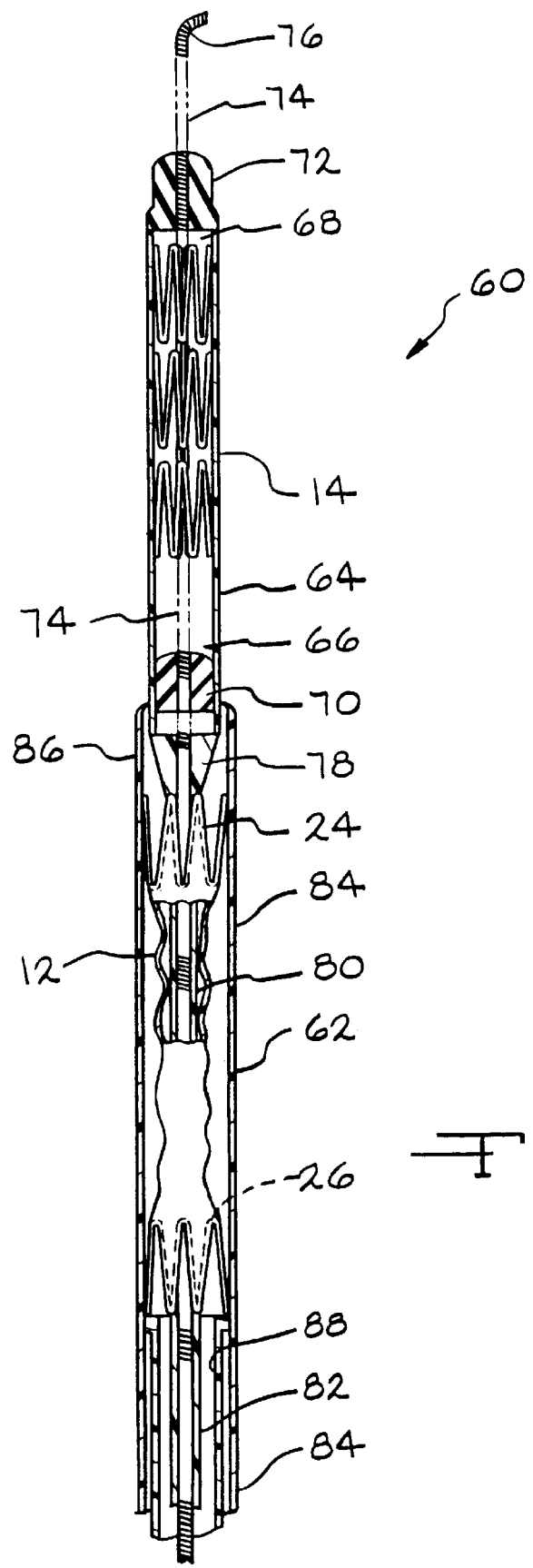
FIG. 3 is a perspective view of a portion of the delivery device for the two-stage stented graft of the present invention.

As shown in FIG. 3, the various embodiments of the stented grafts 10 may also be delivered using a coaxial delivery device 60 of the present invention. Since the stented graft 10 has multiple stages, the size of the delivery device 60 provides for delivery of the various stages of the stented graft 10 through the vasculature and deployment at the treatment site without making multiple entries into the vasculature.

The size of the delivery device needed for placement of a self-expanding stented graft made of serpentine or Z-shaped undulations is determined by several factors. One is the required amount of radial force exerted by the stent. It is known that the radial force of a stent is an increased by increasing the size of the stent wire and/or the number of bends (Fallone et al, 1988, *Invest. Radiol.* 23:370–376). This means that a stent made of a larged diameter wire or having an increased number of bends requires a larger delivery device because the compressed diameter of the stent is also increased. Another factor influencing the required size of the delivery device is the diameter of the recipient blood vessel. To increase the unconstrained diameter of a serpentine or Z-shaped stent, more terminal bends must be added which in turn increases the compressed diameter of the stent. The thickness of the covering material itself has a substantial impact on the compressed diameter of the stented graft and, therefore, the size of the delivery sheath. Finally, the coefficient of friction between the graft and the delivery sheath also affects the required size of the delivery device. Friction is influenced by the graft material, the radial force of the stents, and the length of the stent framework. An increased coefficient of friction may necessitate use of a larger delivery device.

Also described is a method of deployment and endovascular assembly of the two-stage stented graft 10. The double coaxial device 60 comprises two independent first and second coaxial delivery sheaths. The first or proximal sheath 62 provides for the deployment of the first stage anchoring stent 12 shown in FIG. 2A, while the distal or second sheath 64 provides for deployment of the scaffolding stent 14 within the lumen of the deployed anchoring stent. Accordingly, the scaffolding stent 14 is housed inside of the second sheath 64 having a cylindrically shaped side wall extending to opposed open ends 66 and 68. In the assembled delivery device, the open ends 66, 68 are closed by respective stoppers 70 and 72 fixedly mounted on the pusher/holder wire 74. The outer diameter of the second sheath 64 is preferably equal to or smaller than 10-F. The pusher/holder wire 74 is provided having a length sufficient to extend outside the vasculature for manipulation by a physician.

The scaffolding stent 14 surrounds the pusher/holding wire 74 intermediate the stoppers 70, 72 with the second sheath 64 housing the scaffolding stent, supported on the stoppers, which are in a moveable relationship with the second sheath. The distal end of the pusher/holding wire 74 is equipped with a short flexible angled tip 76 to facilitate manipulation within the vasculature. The proximal open end 66 of the second sheath 64 further supports a frusto-conically shaped member 78 that tapers downwardly and inwardly toward the pusher/holder wire 74 and the first sheath 62 of the delivery device 60 to form into a small caliber catheter 80. The frusto-conical member 78 is separate from stopper 70 and is preferably a tapered portion of the second sheath 64 that forms into the catheter 80. The catheter 80 surrounds the pusher/holder wire 74 in a closely-spaced relationship and extends to a proximal end 82 adjacent to a proximal end 84 of the first sheath 62.

The proximal end 66 of the second sheath 64 is received inside the distal open end 86 of the first sheath 62 and in a movable relationship therewith. The anchoring stent 12 is housed inside the first sheath 62 in a surrounding relationship with the catheter 80. The anchoring stent 12 is retained in this position by the frusto-conical member 78 and a pusher tube 88 sized to movably fit inside the first sheath 62.

To assemble the delivery device 60 carrying the disassembled stented graft 10, the catheter 80 is moved through the lumen of the anchoring stent 12 with the first stent 24 of the support frame 22 adjacent to the frusto-conical member 78. The first sheath 62 is then moved over the anchoring stent 12. The scaffolding stent 14 is positioned on the pusher/holder wire 74 intermediate the stoppers 72, 74 and the catheter 80 including the frusto-conical member 78 and the second sheath 64 are moved down the pusher/holder wire 74 until the distal open end 68 of the second sheath 64 abuts the distal stopper 72. The scaffolding stent 14 and the second sheath 64 are now coaxial with the pusher/holder wire 74. In this position, the first sheath 62, anchoring stent 12 and the catheter 80 are coaxial with the pusher/holder wire 74 and the distal open end 86 of the first sheath 62 surrounds the proximal end 64 of the second sheath 64. Finally, the pusher tube 88 is moved over the pusher/holder wire 74 until its distal end is coaxial with and intermediate the distal open end 86 of the first sheath 62 and the proximal end 82 of the catheter 80.

For delivery and deployment of the multi-stage stented graft 10, the delivery device 60 is inserted percutaneously into a blood-vessel. After guiding the delivery device 60 to the desired position, the successive stages of the stented graft 10 are deployed.

First, the first sheath 62 is moved in a proximal direction while the pusher tube 88 and the pusher/holder wire 74 remain stationary. This causes the anchoring stent 12 to deploy with the stents 24 and 26 of the support frame 24 expanding to the size of the lumen of the vessel being treated. Preferably the anchoring stent 12 is of a length sufficient to span a damaged area of the blood vessel with the stents 24, 26 located on opposed sides thereof. The first sheath 62 and the pusher tube 88 are then moved in a proximal direction so that they will not interfere with deployment of the scaffolding stent 14.

Next, the scaffolding stent 14 is moved in a proximal direction until it is centered between the stents 24, 26 of the anchoring stent 12. The scaffolding stent 14 is now deployed by moving the catheter 80 in a proximal direction until the scaffolding stent 14 abuts the stationary stopper 70. The catheter 80 is connected to the second sheath 64 by the frusto-conical member 78 and proximal movement of catheter 80 results in proximal movement of the second sheath 64 and the associated scaffolding stent 14. After proper positioning of the scaffolding stent 14 is confirmed by an imaging technique, the second sheath 64 is moved in a proximal direction to completely unhouse the scaffolding stent 14 which deploys inside the anchoring stent 12.

In that respect, it has been determined that if each of the anchoring stent 12 and the scaffolding stent 14 are deployed inside of the vasculature alone they will each exert a radial force of about 200 units of force, for example. When the scaffolding stent 14 is deployed inside the anchoring stent 14, as described herein, the combined radial force of the two forming the stented graft ais at least about 80% of their combined radial force. This increased radial force is provided without decreasing fatigue life.

Another aspect of the present invention is that when the scaffolding stent is deployed inside the anchoring stent, it is preferred to have the peaks or points of the various stents in a non-aligned relationship as determined in a longitudinal direction. This provides for increased point contact with the inside of the vasculature to increase and enhance the sealing effect of the stented graft 10.

While the method of deploying the stented graft 10 has been described with respect to a two-stage stent, the present invention should not be so limited. The stented graft can be provided with three or more stages deployed one inside the other by housing each inside a sheath that is selectively movable to deploy each stage one at a time in a manner similar to that described with the two-stage stent 10.

It is appreciated that various modifications to the invention concepts described herein may be apparent to those skilled in the art without departing from the spirit and scope of the present invention as defined by the hereinafter appended claims.

What is claimed is:

1. A method of delivering and deploying a multi-stage stent device in one trip into a vasculature, comprising the steps of:
    a) providing a delivery device comprising:
        i) a pusher/holder wire having a length sufficient for manipulation from outside the vasculature, wherein the pusher/holder wire has a distal portion provided with a pair of first and second spaced apart stoppers mounted on the pusher/holder wire;
        ii) a first sheath having a first diameter;
        iii) a second sheath having a second diameter less than the first diameter of the first sheath; and
        iv) a catheter having a third diameter less than the first and second diameters, wherein a distal end of the catheter is connected to a proximal end of the second sheath; and
    b) positioning a first stent device housed inside the first sheath;
    c) positioning a second stent device surrounding the pusher/holder wire and intermediate the first and second spaced apart stoppers;
    d) assembling the delivery device by moving the second sheath over the second stent device and supported on at least one of the first and second stoppers and in a movable relationship therewith, and by moving the catheter through the first stent device housed inside the first sheath;

e) moving the delivery device through the vasculature to position the first stent device at a treatment site;

f) moving the first sheath in a proximal direction while the pusher/holder wire and the catheter remain stationary to thereby deploy the first stent device at such time as the first sheath is removed from its housing relationship with the first stent device;

g) moving the pusher/holder wire and the catheter connected to the second sheath in a proximal direction until the second stent device is properly positioned with respect to, and at least partially inside of, the first stent device; and h) moving the catheter and the associated second sheath in a proximal direction while the pusher/holder wire remains stationary to thereby deploy the second stent device at such time as the second sheath is removed from its housing relationship with the second stent device.

2. The method of claim 1 including providing the first stent device comprising first and second spaced apart stents connected to each other by at least one connecting wire.

3. The method of claim 2 including providing the second stent device having a length such that it fits between the first and second stents of the first stent device.

4. The method of claim 1 including providing the first stent device having a covering graft material.

5. The method of claim 4 including selecting the graft material from the group consisting of polyester, polytetrafluoroethylene, urethane, nylon, lycra and a veneous material.

6. The method of claim 1 including the second stent device comprising at least two stents connected together.

7. The method of claim 1 including providing the pusher/holder wire having flexible distal tip.

8. The method of claim 1 including providing a proximal end of the second sheath surrounded by a distal end of the first sheath in the assembled delivery device.

9. The method of claim 1 wherein the first and second stent device are of Nitinol.

10. The method of claim 1 including providing the first stent device comprising a hollow thermoplastic tube.

11. The method of claim 10 wherein the hollow tube is provided with at least one stent at one of its ends.

12. The method of claim 1 wherein the first stent device and the second stent device comprise stents having peaks or points, wherein when the first stent device and the second stent device are deployed the peaks or points of the stents of the first stent device are positioned in a in a non-aligned relationship with the peaks or points of the stents of the second stent device as determined in a longitudinal direction.

13. The method of claim 1 wherein with the second stent device deployed inside of the first stent device, the combined stent devices exert a radial force of at least about 80% of their combined individual radial forces.

* * * * *